United States Patent
Jeanne et al.

(10) Patent No.: US 9,996,917 B2
(45) Date of Patent: Jun. 12, 2018

(54) DATA ADMINISTRATION SYSTEM AND METHOD

(75) Inventors: Vincent Jeanne, Eindhoven (NL); Maarten Peter Bodlaender, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 195 days.

(21) Appl. No.: 14/237,570

(22) PCT Filed: Aug. 8, 2012

(86) PCT No.: PCT/IB2012/054031
§ 371 (c)(1),
(2), (4) Date: Feb. 7, 2014

(87) PCT Pub. No.: WO2013/027141
PCT Pub. Date: Feb. 28, 2013

(65) Prior Publication Data
US 2014/0205165 A1    Jul. 24, 2014

Related U.S. Application Data

(60) Provisional application No. 61/525,867, filed on Aug. 22, 2011.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0077* (2013.01); *A61B 5/117* (2013.01);
(Continued)

(58) Field of Classification Search
CPC ..... A61B 5/0077; A61B 5/117; A61B 5/0075; A61B 5/02405; A61B 5/02416;
(Continued)

(56) References Cited

U.S. PATENT DOCUMENTS 6,567,775 B1 * 5/2003 Maali et al. .................. 704/231
8,649,562 B2   2/2014 De Haan et al.
(Continued)

FOREIGN PATENT DOCUMENTS

JP    2003141086    5/2003
JP    2007252803    10/2007
(Continued)

OTHER PUBLICATIONS

Anand, N., et al.; A pervasive wireless sensor network approach for monitoring vital signs; 2011; Proc. of Natl. Conf. on Recent Trends in Engineering Sciences; pp. 355-362.
(Continued)

*Primary Examiner* — Li Liu (57) ABSTRACT

The present invention relates to a data administration system (1a, 1b, 1c) comprising a sensor unit (10) for obtaining image data of at least a body part of a living being (2), a vital sign extraction unit (12) for extracting one or more vital signs of said living being (2) from the obtained image data of said living being (2), a feature extraction unit (14) for extracting one or more features of said living being (2) from the obtained image data of said living being (2), an identification unit (16) for determining the identity of said living being (2) by use of said one or more extracted features of said living being (2), and a data association unit (18) for associating the one or more extracted vital signs of said living being (2) with the determined identity of said living being (2).

16 Claims, 5 Drawing Sheets

(51) Int. Cl.

| | |
|---|---|
| *A61B 5/1171* | (2016.01) |
| *A61B 5/117* | (2016.01) |
| *G06K 9/20* | (2006.01) |
| *G06F 19/00* | (2018.01) |
| *A61B 5/00* | (2006.01) |
| *A61B 5/024* | (2006.01) |
| *A61B 5/1455* | (2006.01) |

(52) U.S. Cl.
CPC .......... *A61B 5/1171* (2016.02); *G06F 19/327* (2013.01); *G06K 9/00288* (2013.01); *G06K 9/00906* (2013.01); *G06K 9/2018* (2013.01); *G06T 7/0016* (2013.01); *A61B 5/0075* (2013.01); *A61B 5/02405* (2013.01); *A61B 5/02416* (2013.01); *A61B 5/14551* (2013.01); *A61B 5/7485* (2013.01); *G06F 19/345* (2013.01); *G06T 2207/30076* (2013.01)

(58) Field of Classification Search
CPC . A61B 5/7485; A61B 5/14551; G06T 7/0012; G06F 19/322; G06K 9/00906; G06K 9/2018; G06K 9/00288
See application file for complete search history.

(56) References Cited

U.S. PATENT DOCUMENTS

| | | | |
|---|---|---|---|
| 2006/0013446 A1 | 1/2006 | Stephens | |
| 2007/0129636 A1 | 6/2007 | Friedman et al. | |
| 2010/0199228 A1 | 8/2010 | Latta et al. | |
| 2010/0245553 A1 | 9/2010 | Schuler et al. | |
| 2012/0022348 A1* | 1/2012 | Droitcour | A61B 5/0507 600/323 |
| 2012/0059268 A1* | 3/2012 | Tupin, Jr. | A61B 5/0002 600/484 |
| 2012/0140068 A1* | 6/2012 | Monroe et al. | 348/143 |
| 2012/0270332 A1 | 10/2012 | Winberger-Friedl et al. | |
| 2013/0001422 A1* | 1/2013 | Lavon et al. | 250/338.1 |
| 2014/0253709 A1* | 9/2014 | Bresch | H04N 7/18 348/77 |
| 2014/0303454 A1* | 10/2014 | Clifton | A61B 5/0205 600/301 |

FOREIGN PATENT DOCUMENTS

| | | |
|---|---|---|
| WO | 2010100593 A1 | 9/2010 |
| WO | 2012140531 A1 | 10/2012 |

OTHER PUBLICATIONS

Benfold, B., et al.; Stable multi-target tracking in real-time surveillance video; 2011; IEEE Conf. on Computer Vision and Pattern Recognition; pp. 3457-3464.

Chekmenev, S. Y., et al.; Non-contact, Wavelet-based Measurement of Vital Signs using Thermal Imaging; 2006; ICGST Int'l Journal on Graphics, Vision and Image Processing; 6(2)25-30.

Dalal, N., et al.; Histograms of Oriented Gradients for Human Detection; 2005; Intl. Conf. on Computer Vision & Pattern Recognition; pp. 886-893.

Garcia-Martin, A., et al.; Robust Real Time Moving People Detection in Surveillance Scenarios; 2010; Advanced Video and Signal Based Surveillance (AVSS); pp. 241-247.

Liao, W-H., et al.; Video-based Activity and Movement Pattern Analysis in Overnight Sleep Studies; 2008; ; Intl. Conf. on Computer Vision & Pattern Recognition; pp. 1-4.

Luber, M., et al.; Learning to Detect and Track People in RGBD Data; 2011; Workshop on RGB-D Cameras; pp. 1-2.

Tan, K. S., et al.; Real-time vision based respiration monitoring system; 2010; Symposium on Communication Systems Networks and Digital Signal Processing (CSNDSP); pp. 770-774.

Verkruysse, W., et al.; Remote plethysmographic imaging using ambient light; 2008; Optics Express; 16(26)21434.

Viola, P., et al.; Robust Real-time Object Detection; 2001; International Journal of Computer Vision; pp. 1-25.

Xiao, Y., et al.; An Algorithm for Processing Vital sign Monitoring Data to Remotely Identify Operating Room Occupancy in Real-time; 2005; Anesth. Analg.; 101: 823-829.

Yao, J., et al.; Multi-layer Background Subtraction Based on Color and Texture; 2007; CVPR Visual Surveillance Workshop (CVPR-VS); pp. 1-8.

Dobromir Todorov: "Exerpt", In: "Mechanics of User Identification and Authentication", Jun. 18, 2007; Auerbach Publications, p. 5.

Massimo Tistarelli, et al.: "Excerpt", In: "Handbook of Remote Biometrics for Surveillance and Security", Jun. 2, 2009, Springer, p. 83.

\* cited by examiner

DATA ADMINISTRATION SYSTEM AND METHOD

CROSS REFERENCE TO RELATED APPLICATIONS

This application is a national filing of PCT application Serial No. PCT/IB2012/054031, filed Aug. 8, 2012, published as WO 2013/027141 A2 on Feb. 28, 2013, which claims the benefit of U.S. provisional application Ser. No. 61/525,867 filed Aug. 22, 2011, which is incorporated herein by reference.

FIELD OF THE INVENTION

The present invention relates to a data administration system and method. Further, the present invention relates to a processor and a processing method for use in such a data administration system. Still further, the present invention relates to a computer program for implementing said processing method.

BACKGROUND OF THE INVENTION

Camera-based vital signs monitoring can measure heart-rate, respiration and oxygenation, SpO2 values and actigraphy unobtrusively from a distance. Traditional contact sensors for measuring heart-rate, respiration, SpO2 and actigraphy are attached to the subject (i.e. a living being, particularly a human being like a person, but possibly also an animal). Inherently the vital signs values produced by these sensors are associated with a subject ID, i.e. an identifier of the subject that uniquely identifies the subject. For instance, in a hospital environment, from day one on which a patient is in the hospital the nurse attaches the sensor to the patient, and the measured vital signs are then associated to the patient's name and bed number. One of the main advantages of camera-based vital signs monitoring over on-body sensors is the high ease-of-use since there is no need to attach a sensor to the living being, but the camera just needs to be directed to the living being.

Since camera-based vital signs monitoring is performed in a contactless way, it is unclear how to associate the values measured to the identity of the subject. As an example, in hospitals no system is able to detect that the vital signs measured from one patient lying in a bed at time t0 are still the vital signs of that same patient at time t0+t. A new patient might be there or patients might have voluntarily/involuntarily exchanged their beds.

Due to the constant patient flow, it is not desirable to have a fixed association based on patient's bed location. This could clearly lead to a confusion of medical data which is not acceptable. It is also not a preferred solution to attempt to "track" a patient based on its vital parameters only because of the extremely high probability of mismatch with another patient. Due to the limited range of values of the vital signs measured is very likely to find two persons having at one point in time the same parameters. Further, identification based on vital signs is considered unsuitable in many application due to the fact that the evolving health condition, e.g. of a patient in a hospital, changes the vital signs, making them less suitable for identification of the patient.

SUMMARY OF THE INVENTION

It is an object of the present invention to provide a data administration system and method enabling the automatic association of remotely measured vital signs with the identity, and potentially further data, of the correct living being.

In a first aspect of the present invention a data administration system is presented comprising:
 a sensor for obtaining image data of at least a body part of a living being,
 a vital sign extraction unit for extracting one or more vital signs of said living being from the obtained image data of said living being,
 a feature extraction unit for extracting one or more features of said living being from the obtained image data of said living being,
 an identification unit for determining the identity of said living being by use of said one or more extracted features of said living being, and
 a data association unit for associating the one or more extracted vital signs of said living being with the determined identity of said living being.

In a further aspect of the present invention a processor for use in a data administration system is presented comprising:
 a vital sign extraction unit for extracting one or more vital signs of a living being from obtained image data of said living being,
 a feature extraction unit for extracting one or more features of said living being from the obtained image data of said living being,
 an identification unit for determining the identity of said living being by use of said one or more extracted features of said living being, and
 a data association unit for associating the one or more extracted vital signs of said living being with the determined identity of said living being.

According to further aspects of the present invention a corresponding data administration method and a processing method are presented.

Preferred embodiments of the invention are defined in the dependent claims. It shall be understood that the claimed proposed processor, the proposed methods and the proposed computer program have similar and/or identical preferred embodiments as the claimed data administration system and as defined in the dependent claims.

The present invention is based on the idea to use obtained image data of a living being (herein also generally called subject, which generally include human beings and animals) not only for the extraction of vital signs but additionally for the extraction of features of the living being that allow to uniquely identify the living being. The vital signs extracted from the image data of that particular living being can then be associated with the determined identity of the living being. Thus, the image data obtained by the sensor unit, e.g. a video camera, have a double function, and no additional means are required to identify the living being separately, which would also require means that ensure that the vital signs are associated to the correct identity since the identity is determined by use of different means and from different data.

The present invention enables a simple, fast and reliable association of the identity of a subject, e.g. a patient ID, to vital signs measured for that subject. It can thus be ensured that all vital signs captured using a sensor unit, particularly a video camera, are associated to a known identity which makes it possible to find back which vital signs belong to which subject and build reliable database, e.g. a medically acceptable record-keeping of patient data.

It shall be noted that in this context the determination of the "identity" of a subject, e.g. a person shall be understood to include not only the determination of the full or real identity (e.g. the name of a person and/or the ID under which a person is registered, for instance in a database of a hospital or a security area), but shall also include a partial identification. Such a partial identification, i.e. the determination of a partial or incomplete identity may, for instance, be the verification that the subject (e.g. a patient) is still the same, without attempting to provide a full identity.

According to a preferred embodiment the proposed data administration system further comprises an image area detection unit for detecting one or more image areas within images of said image data, an image area covering an area of the size of one or more body parts of a single living being or a complete living being, wherein said sensor unit is configured to obtain images of a scene potentially comprising more than one living beings, wherein said vital sign extraction unit is configured to extract one or more vital signs of a living being from the image data of an image area comprising at least a body part of a living being, and wherein said feature extraction unit is configured to extract one or more features of said living being from the image data of an image area comprising at least a body part of a living being. This embodiment is, for instance, used in the waiting area of a hospital where many new patients arrive but have to wait before they are treated. After identification at the registration desk they can be observed and their vital signs can be measured from a distance to see if the vital signs of a certain patient deteriorate to an extent requiring immediate attention and treatment. Even if a patient moves in the waiting area he can be tracked since images are taken constantly or at regular intervals (or images are evaluated at regular intervals) including the determination of the identity to avoid that vital signs measured from image data obtained from a certain image area are assigned to a wrong patient (e.g. because patients have exchanged their seats).

According to another preferred embodiment the proposed data administration system further comprises a storage unit for storing a database of identities of living beings including one or more features of said living beings, wherein said identification unit is configured to determine the identity of said living being by comparison of said one or more extracted features of said living being with the features stored in said database of identities. This database may, for instance, be the patient record database of a hospital or a doctor in a private practice. The present invention thus enables that all the data stored in the database can be immediately be provided, e.g. to a nurse at the registration desk or a doctor in the emergency department.

Preferably, said storage unit is configured to store said one or more extracted vital signs of said living being in a database entry of the determined identity. This enables to keep all data of a living being together for future use. The storage unit may, for instance, be a central storage like a data management system of a hospital using large hard disks for storing all patient data.

Preferably, said sensor unit includes a camera, in particular a video camera for obtaining image data in the visual and/or infrared wavelength range. Generally, any kind of sensor can be used that provides image data from which vital signs and features of the living being useful for identification can be extracted. In case of a video camera the image data comprise a sequence of images. The video camera can be a digital video camera of a traditional kind. It is possible to obtain the image data from the entire visible spectrum of light. Alternatively, the camera can be adapted to a narrower band of wavelengths or to specific wavelengths that are relevant for the vital signs to be measured, as for example an infrared camera or an RGB camera. For instance, if blood oxygenation shall be measured a combination of the green, red and infrared wavelength band is of main interest.

A further alternative for a camera is a terahertz camera. The terahertz camera is adapted to an electromagnetic spectrum which is located between microwaves and near-infrared regions of the electromagnetic spectrum. This specific camera has the advantage of measuring through different types of material, as for example clothes. Further, it is measuring more deeply through skin and is less sensitive to motions of the examined living being. Therefore, the terahertz camera provides a very robust way for obtaining high quality image data useful for vital sign extraction but also for feature extraction.

In addition, depending on the application, an additional light source including the wavelengths used for the desired measurement can be used to improve the quality of the image data, particularly with respect to vital sign extraction. It is an advantage that such video cameras are highly available and very cost effective. A further advantage is that the image data obtained by the video camera contain a plurality of information which can be analyzed over time as to identify the body parts correctly and to adapt to changes in a determined scene, e.g. to light conditions.

Advantageously, said sensor unit is configured to obtain image data from one or more predetermined measurement areas, a measurement area covering an area of the size of one or more body parts of a single living being or a complete living being, in particular to obtain image data from only those measurement areas including a body part of a living being. This reduces the efforts for vital sign extraction and feature extraction since the amount of image data is considerably reduced. For instance, in a waiting room of a hospital the measurement areas could be linked to the waiting seats.

In an even further improved embodiment the sensor unit obtains image data from only those measurement areas that includes a body part of a living being (including the situation that the measurement area includes a complete living being). For instance, in the above mentioned example only from those areas of waiting seats that are occupied by a patient waiting for treatment image data are acquired. For this purpose means are provided in the sensor unit to determine which measurement areas are "occupied" by a living being. This means may include conventional means for object/person detection, means for movement detection and/or means for foreground/background detection. Thus, the processing time and efforts are further reduced. For instance, if the sensor unit is able to obtain images of a whole waiting area, but only a single patient is waiting the image data will preferably be obtained only from the measurement area where said single patient is present.

Preferably, said vital sign extraction unit is configured to determine one or more regions of interest of said living being and to extract one or more vital signs from said one or more regions of interest. The particular regions detected much depend on the kind of vital sign to be extracted. These vital signs include, but are not limited to blood oxygenation, pulse, blood pressure, heart rate variability, respiratory rate, depth of anesthesia and/or hypo- and hypervolemia. The vital signs extraction unit is generally able to derive corresponding vital signs (also called bio metrical signals). Depending on the vital signs to be extracted different extraction techniques are used. For instance, pulse, heart rate variability and respiratory rate are periodical phenomena. These phenomena can be extracted by extraction techniques for periodic changes in the acquired image data. The phenomena blood oxygenation and blood pressure are not necessarily of a periodic kind. Hence, a more static extraction technique is needed.

Preferably, said vital sign extraction unit is configured to extract one or more vital signs from the obtained image data of said living being by a breathing monitoring method, a photo-plethysmography method and/or an actigraphy monitoring method. A method and device for breathing monitoring is, for instance, described in the European patent application having the application number EP 11162384 filed by the applicant on Apr. 14, 2011. Basically it describes how respiration can be measured from displacements of the chest or belly/back. Such displacements can be recognized in the image data obtained according to the present invention.

A method to measure skin colour variations, called Photo-Plethysmographic imaging (PPG), is described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while processing calculates the pixel average over a manually selected region (typically part of the cheek in this system). By looking at periodic variations of this average signal, the heart beat rate and respiratory rate can be extracted.

Thus, the pulsation of arterial blood causes changes in light absorption. Those changes observed with a photodetector (or an array of photodetectors) form a PPG (photo-plethysmography) signal (also called, among other, a pleth wave). Pulsation of the blood is caused by the beating heart, i.e. peaks in the PPG signal correspond to the individual beats of the heart. Therefore, a PPG signal is a heartbeat signal in itself. The normalized amplitude of this signal is different for different wavelengths, and for some wavelengths it is also a function of blood oxygenation.

To improve robustness of heart rate calculation, it is beneficial to use more than one PPG signal, in particular signals obtained at different wavelengths in such a way, that the difference of normalized amplitudes is maximized. Division of one signal by the other helps to eliminate distortions present in both signals.

Another field of application of the present invention is SpO2 estimation. Thus, preferably, the processing means is adapted for extracting a SpO2 signal from said at least one combined color signal by extracting at least two PPG signals at different wavelengths and determining a SpO2 signal from said at least two PPG signals.

SpO2 estimation is based on the ratio of the normalized amplitudes of PPG signal at two different ranges of wavelengths (one at red and the other at infra-red part of the spectrum):

$$RR = \frac{\frac{AC_{IR}}{DC_{IR}}}{\frac{AC_R}{DC_R}}.$$

From this "ratio of ratios", the SpO2 value is obtained using experimentally defined constants $C_1$ and $C_2$ $$SpO_2 = C_1 - \frac{C_2}{RR}.$$

The biometrical signal being directly measured is the PPG signal. SpO2 is calculated from two PPG signals. Similarly, other mentioned signals/properties (respiration, depth of anesthesia, etc.) are also derivatives of the PPG signal.

Video Actigraphy herein means body motion analysis. Such a video actigraphy method is described in Liao and Yang "Video-based Activity and Movement Pattern Analysis in Overnight Sleep Studies", Pattern Recognition, 2008, ICPR 2008.

In a preferred embodiment said feature extraction unit is configured to extract one or more features of said living being from the obtained image data of said living being by at least one feature extraction method out of a group of feature extraction methods including:
i) an object recognition method for recognizing features from face, chest or other body parts,
ii) a biometric feature extraction method for extracting biometric features, in particular height, width, body contour, body volume, iii) a gate analysis method for gate pattern recognition,
iv) a texture recognition method for recognizing texture features,
v) a color recognition method for recognizing color features. Methods to be used for such a feature extraction from images of a living being are generally known and available.

Object recognition methods are, for instance, described in Navneet Dalai, Bill Triggs, "Histograms of Oriented Gradients for Human Detection," CVPR, vol. 1, pp. 886-893, 2005 IEEE Computer Society Conference on Computer Vision and Pattern Recognition (CVPR'05)—Volume 1, 2005. Another method is described in Paul Viola and Michael Jones, "Robust Real-time object detection", International Journal of Computer Vision, 2001. Still another method is described in B Benfold and I D Reid, "Stable Multi-Target Tracking in Real-Time Surveillance Video", Proceedings Computer Vision and Pattern Recognition (CVPR), Colorado Springs, June 2011.

A method for detecting people using 3D are, for instance, used in the commercially available sensor "Kinect" described e.g. in US 2010/0199228 A1. A further method is described in Matthias Luber, Luciano Spinello, Kai Arras, "Learning to Detect and Track People in RGBD Data", RGB-D Workshop on RGB-D Cameras 2011.

A method for people detection based on motion segmentation is described in Garcia-Martin, A., Martinez, J. M., "Robust Real Time Moving People Detection in Surveillance Scenarios", Advanced Video and Signal Based Surveillance (AVSS), August 2010.

A method for foreground/background detection is described in Jian Yao and Jean-Marc Odobez, "Multi-Layer Background Subtraction Based on Color and Texture", Proc. CVPR Visual Surveillance workshop (CVPR-VS), Minneapolis, June 2007.

In an embodiment said sensor unit comprises a plurality of sensors for obtaining image data from a predetermined monitored area. This embodiment allows the tracking of living beings in said monitored area, e.g. if patient walk through a hospital.

Further, different units, e.g. the vital signs extraction unit and the feature extraction unit, may receive image data from different sensors. Different sensors can also differ in their position and/or their specifications. Still further, in an embodiment, they can be used for obtaining image data from different angles and/or with different wavelength of light, wherein all or selected image data from said plurality of sensors are used for vital signs and/or feature extraction. In this way, more information is provided for examining the living being so that the accuracy of the examination can be improved.

Still further, in an embodiment the data administration system further comprises an audio sensor, in particular a microphone, for obtaining audio data of said living being, wherein said identification unit is configured to determine the identity of said living being by use of said one or more extracted features and the obtained audio data of said living being. The audio data can, for instance, be used for voice recognition. In itself such technique is, most likely, not fully reliable but associated with the other identification method it can improve the overall accuracy.

Preferably, a notification means is for notifying a predetermined person or service in case of predetermined conditions, in particular in case said one or more vital signs of a living being show that the living being is deteriorating. Said notification means may include an emergency call unit to inform a doctor or an emergency center.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
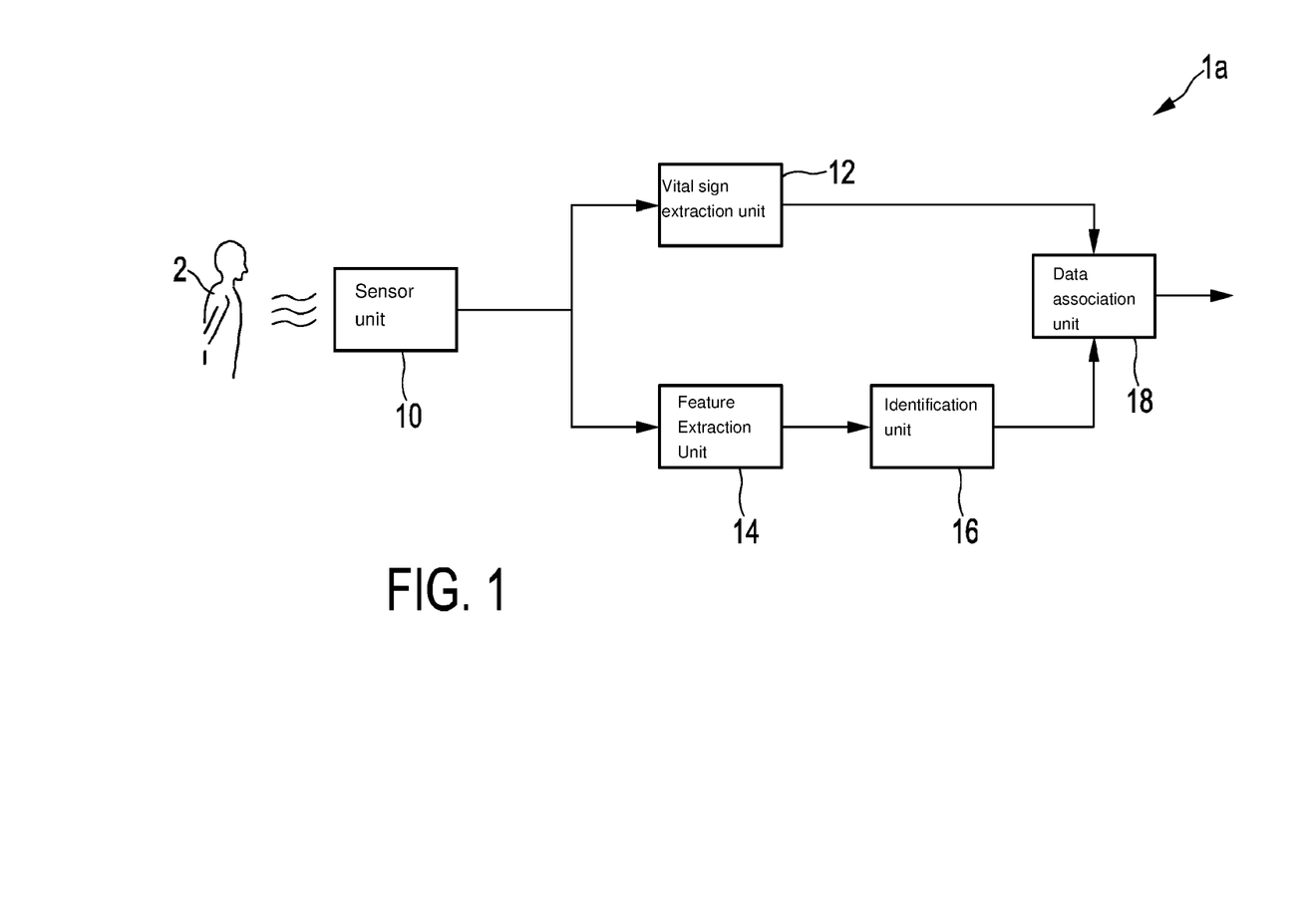
FIG. 1 shows a schematic diagram of a first embodiment of a data administration system according to the present invention.

FIG. 1 shows a schematic diagram of a first embodiment of a data administration system 1a according to the present invention. The data administration system 1a comprises a sensor unit 10 for obtaining image data of at least a body part of a living being 2. Said sensor unit 10 may, for instance, be a video camera for capturing images of the whole body or at least the upper part of the body of a patient 2 in a hospital. The data administration system 1a further comprises a vital sign extraction unit 12 for extracting one or more vital signs of said living being 2 from the obtained image data of said living being 2. Said vital sign extraction unit 12 may, for instance, be a PPG (photo-plethysmograph) device that extracts the heat rate or an SpO2 signal from the images of a patient 2, said images comprising at least image data of parts of the skin, e.g. of the cheeks, of a patient.

The data administration system 1a further comprises a feature extraction unit 14 for extracting one or more features of said living being 2 from the obtained image data of said living being 2. Said feature extraction unit may, for instance, be an object recognition unit that recognizes features from body parts such as the face or chest by which a living being can be uniquely characterized and identified. These one or more extracted features are then used in an identification unit 16 for determining the identity of the living being 2. Finally, in a data association unit 18 the one or more extracted vital signs of the living being are then associated with the determined identity of the living being.

Thus, the present invention enables the automatic association of remotely measured vital signs with an identity of a living being, such as a patient identity, and reliably avoids that vital signs are assigned to a wrong living being. This idea can be applied in various contexts. For instance, in a medical context, such as in a hospital, the present invention enables a medically acceptable record-keeping of patient data and avoids the confusion of patients' vital signs which in an extreme case could have a lethal outcome. Further, the present invention enables tracking of vital signs of patients, even before patients have been registered by the hospital, potentially detecting patients that are deteriorating while waiting. The present invention can further be applied in all situations with one or more unknown people, such as security areas (e.g. at an airport or the entrance of a building), home monitoring, public buildings, etc.

The operation of this embodiment of the data administration system 1a shall be explained by way of a non-limiting example. First, by use of the sensor unit 10 a set of consecutive images is acquired. The acquired images are, for instance, e captured with a camera that is sensitive to the wavelengths that are relevant for the vital signs to be extracted. For breathing monitoring the sensor unit 10 needs to be sensitive to at least one wavelength in the visible an/or in the infrared part of the spectrum (which will allow day and night sensing). For extracting vital signs from remote PPG signals the sensing unit 10 is to be sensitive to at least two wavelengths in the visible part of the spectrum with an option to use at least one wavelength in the infrared part of the spectrum, said option allowing SpO2 signal extraction and night monitoring. For actigraphy monitoring the sensor unit 10 needs to be sensitive to at least one wavelength in the visible and/or the infrared part of the spectrum (again allowing day and night monitoring).

Optionally, an additional light source can be used to illuminate the living being 2 with radiation in the wavelength range for which the sensor unit 10 is sensitive and which includes the wavelengths which are required for extracting the desired vital signs.

For extraction of vital signs preferably at least one region of interest (ROI) is detected in one or more images of said image data, which region of interest is selected such that it shows details or body parts of the living being from which the desired vital signs can be extracted. For breathing monitoring the ROI comprises the chest area, particularly if the measurement is performed using a motion pattern analysis algorithm as, for instance, described in European patent application EP 11162384 or "Real-Time Vision Based Respiration Monitoring System", K. S. Tan, R. Saatchi, H. Elphick, and D. Burke, CSNDSP 2010. For vital signs that can be derived from remote PPG (such as heart rate, heart rate variability, pulse transit time, respiration and SpO2) the ROI comprises at least one portion of the living being's body containing visible skin, such as the cheeks. For actigraphy monitoring the ROI generally comprises the full body (or at least the biggest part of the body) of the living being.

The detection of the ROI can be performed by use of one or more methods of a group of methods including (pre-trained) object detection (face, chest or other body parts), detection based on color information (e.g. skin parts), use of a body model based on 3D information obtained using a 3D camera or a stereo vision system, foreground and/or background detection.

The extraction of the vital sign(s) from the ROI is performed as described above by use of a known method, in particular by a known breathing detection method, actigraphy monitoring method and/or PPG method. Details of such methods can be found in the above-mentioned documents so that these methods are not further explained here in detail.

The obtained image data are further used for extracting one or more features of the living being. In an embodiment a set of visual markers (also called identifiers) is extracted. These markers include, but are not limited to, features extracted from the face, chest, and/or other body parts for object recognition; biometric features (e.g. height, width, body contours, body volume obtained from 3D-information); a gate pattern for personal recognition based on a gate analysis; texture features (clothes, hair, etc.) for texture recognition; color features (e.g. skin color detection, hair color detection).

Preferably, at least one of these features is stored in a vector that is used by the identification unit 16 for identifying a living being. Preferably, such a vector comprises several features which are commonly used for identification to increase accuracy and reliability of the identification.

The identity check performed in the identification unit 16 can be performed by a use of a best match approach by which a best match with an identity registered in the data administration system is searched. For instance, a storage unit 22 may be provided, as shown in the embodiment of the data administration system 1b depicted in FIG. 2. This storage unit 22 may store a database of identities of living beings including one or more features of said living beings, e.g. storing a vector of one or more features of patients that have ever been registered to a hospital using said data administration system. The vector of actually extracted one or more features of a living being, e.g. a new patient entering the hospital, is then used for comparison with vectors stored in said database 22.

Figure 2:
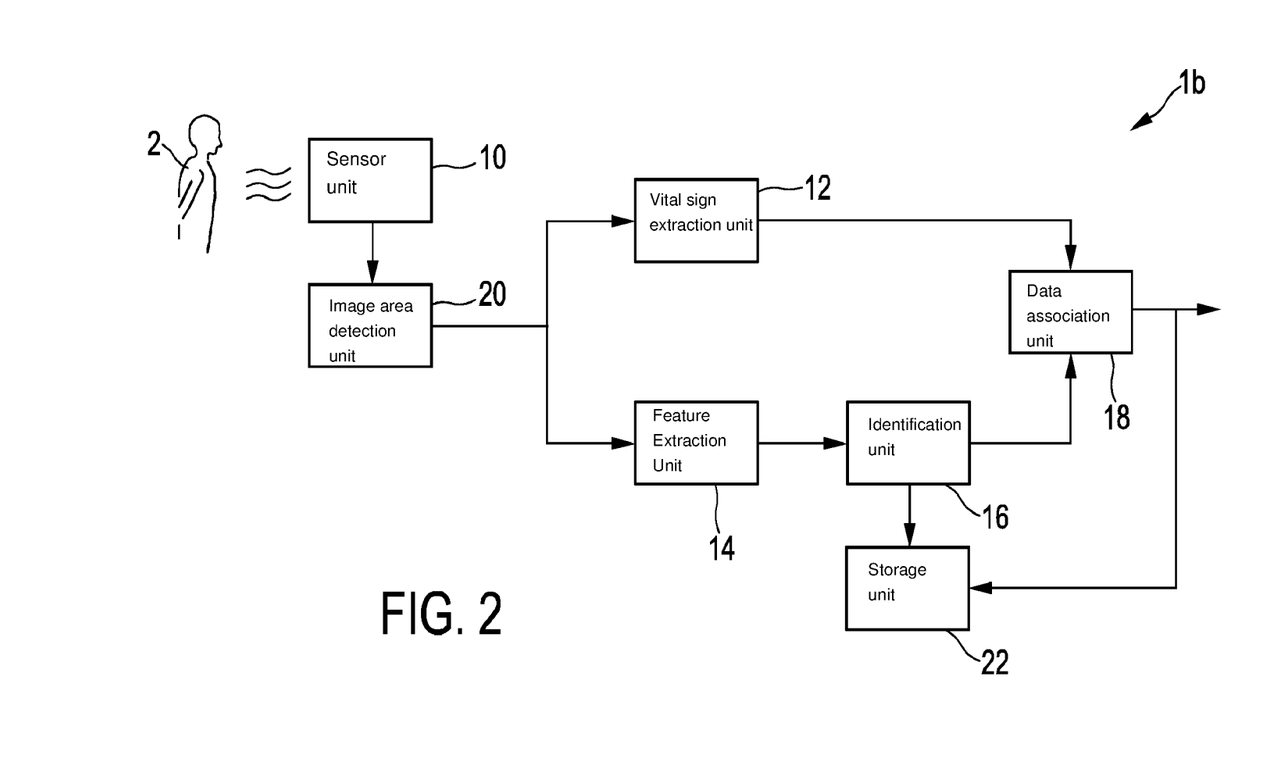
FIG. 2 shows a schematic diagram of a second embodiment of a data administration system according to the present invention.

In an implementation, for instance, a threshold is used to check if the match is significant enough. This operation is performed to ensure that several persons do not use the same identity. If the significance of the best match is below the predetermined threshold, the person from which the current vector of one or more features has been extracted is considered as new and a new identity is created as will be explained below, i.e. a new vector will be entered in the database stored in the storage unit 22.

The identity check can also be performed in the identification unit 16 by a use of a manual identification for the first time: a new living being is present from whom vital signs have been extracted. For instance, in a hospital the patient is asked to register and identify himself/herself at the registration desk so that vital signs that have already been extracted during the time while the patient was waiting can be associated with the correct patient.

Still further, the identity check can also be performed in the identification unit 16 by a use of an automatic identification for the first time: a new person is thus automatically found. For instance, from the image data the visual markers are extracted. If no good match (distance<threshold) is found with the identities already stored, then the person is considered as new and a new identity is created.

In one embodiment it is assumed that the "first time" identification is manually performed by a user, e.g. a nurse, at a dedicated location (e.g. the admittance or registration desk). The registration of the identity is based on the user input (patient name, social security number, insurance company, . . . ) along with at least one of the features extracted by the feature extraction unit 14 as described above. This embodiment allows the recording of patients before their actual registration in the identity database and/or the hospital data administration system. For instance, this case is expected to happen in the waiting rooms of an emergency department of a hospital. It will allow the medical team to have medical data of a patient prior to any auscultation.

In the embodiment of the data administration system 1b shown in FIG. 2, all vital signs that have been associated (tagged) with the correct living being are stored along with their identifier (e.g. patient ID which may be a number assigned to the identity in a central database stored in the storage unit 22) are stored in a central unit to produce medical reports or medically relevant data (e.g. arrhythmia detection, apnea, . . . ). Said central unit may be the storage unit 22 or a different unit, e.g. the central data administration system of a hospital. It should be noted in this context that the storage unit 22 may also be provided in other embodiments of the proposed data administration system.

Figure 3:
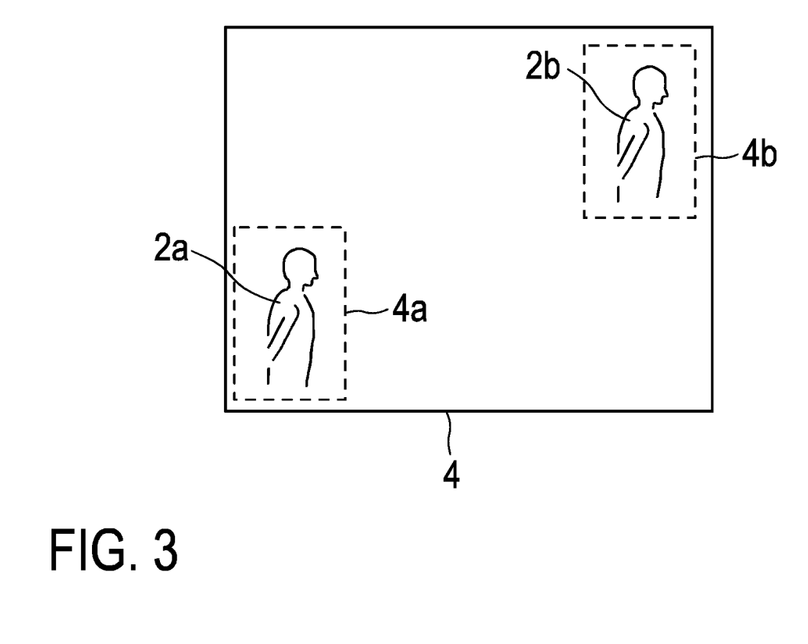
FIG. 3 shows a diagram illustrating an operation of the measurement area detection unit.

In the embodiment of the data administration system 1b shown in FIG. 2, an additional image area detection unit 20 is provided for detecting one or more image areas within images of the image data obtained by the sensor unit 10. This is illustrated in the diagram depicted in FIG. 3. FIG. 3 shows an image 4 which has been recorded from a scene comprising two persons 3a, 3b. The image area detection unit 20 thus detects image areas 4a, 4b which each cover an area of the size of at least one or more body parts, here in this example of the complete body, of a single person. In other words, the image area 4a covers the area of the whole person 3a, and the image area 4b covers the whole area of the person 3b. For such image area detection in images, e.g. taken by a still camera or a video camera, various detection techniques are available that can be used for this purpose here, said available detection techniques including a detection based on a Viola and Jones object detector framework, detection based on 3D-information obtained by a 3D camera or stereo vision system, detection based on motion segmentation, and detection based on foreground/background detection.

The use of image area detection provides the advantage that the vital sign extraction and/or the feature extraction processes only the image data from those image areas 4a, 4b for vital sign extraction and feature extraction, respectively, rather than processing the complete image data of complete images 4. This considerably reduces the processing time and the storage space. Furthermore, per image area a vector of features can be obtained and assigned to said image area, for which the identity is determined by the identification unit 16.

Figure 4:
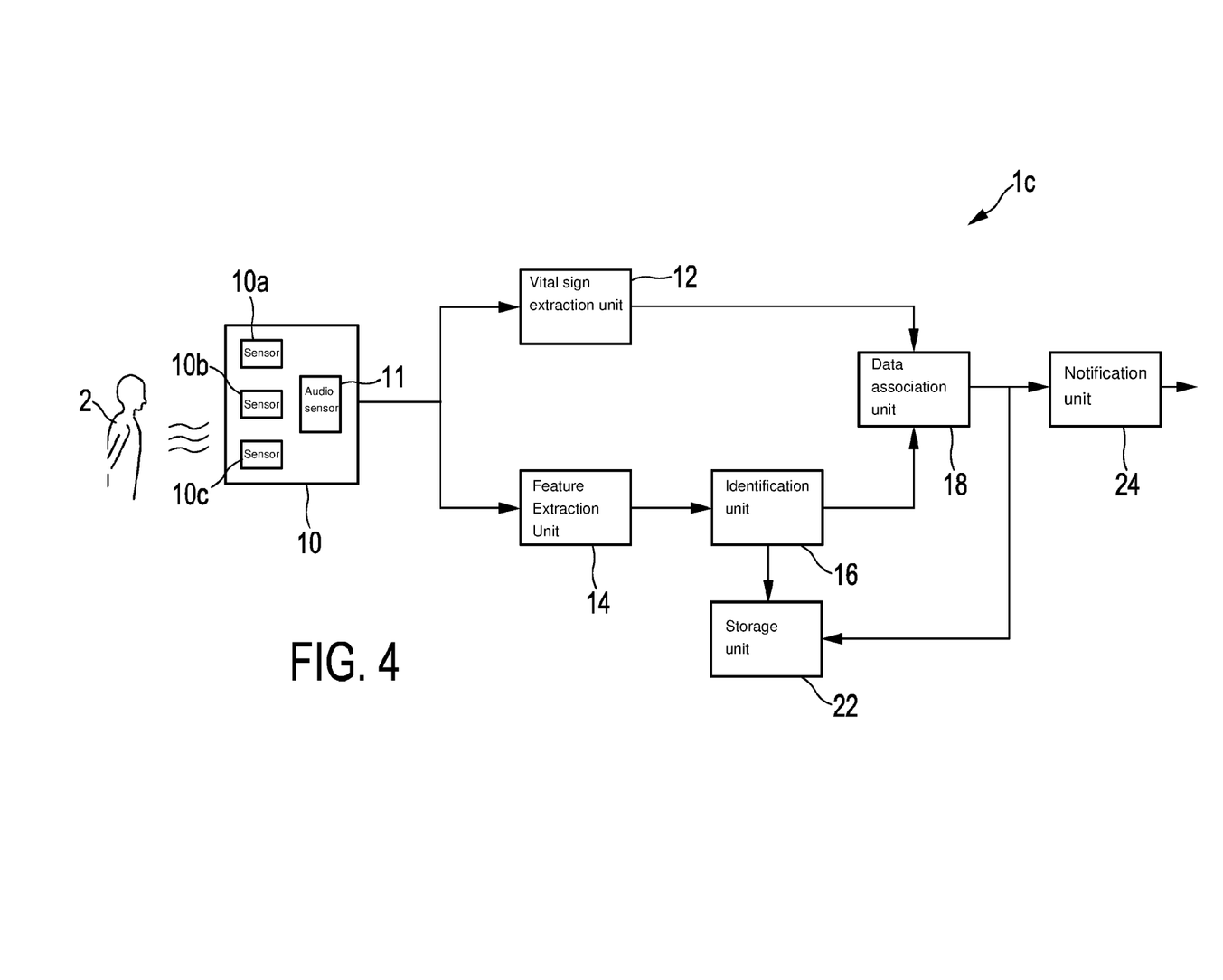
FIG. 4 shows a schematic diagram of a third embodiment of a data administration system according to the present invention.

FIG. 4 shows a third embodiment of a data administration system 1c according to the present invention. In this embodiment the sensor unit 10 comprises not only a single sensor, such as a single video camera or a single image sensor, but comprises a plurality of sensors 10a, 10b, 10c. These sensors 10a, 10b, 10c may be identical and may be used to obtain image data in parallel which are then all processed to increase the accuracy of the extraction of vital signs and features of a living being. For instance, the image data may be used in an averaging process before they are used for vital signs and feature extraction. Alternatively, the best image data may be selected for said processing.

Figure 5:
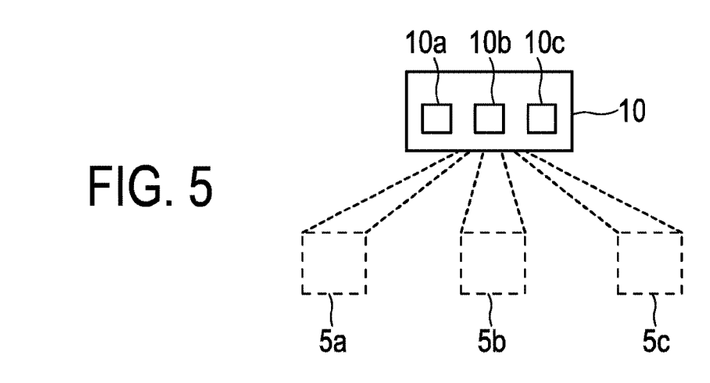
FIG. 5 shows a diagram illustrating the detection of various measurement areas.

In a different embodiment, as depicted in FIG. 5, to each sensor 10a, 10b, 10c a certain measurement area 5a, 5b, 5c is assigned, from which each sensor 10a, 10b, 10c obtains image data. Such a management area 5a, 5b, 5c covers an area of the size of one or more body parts of a single living being or a complete living being, in particular to obtain image data from only those measurement areas including a body part of a living being. Such a measurement area may, for instance, be assigned to the chairs of a waiting area in a hospital, i.e. only in case a chair is occupied by a patient image data are recorded by the associated sensor from the measurement area of said chair, and only in this case the obtained image data are then further processed for vital signs extraction and feature extraction as described above. This embodiment also saves processing time and storage space for storing image data since from unoccupied chairs no image data are preferably obtained at all (or are at least not further stored and/or processed).

It should be noted in this context that for monitoring two or more measurement areas 5a, 5b, 5c as depicted in FIG. 5 it is not necessarily required to have a sensor unit 10 comprising a single sensor 10a, 10b, 10c for each measurement area, but it is also possible that the sensor unit 10 is adapted for only monitoring predetermined measurement areas and/or obtaining image data from only those measurement areas. For instance, in an embodiment the sensor unit 10 may be adapted to sweep over the measurement areas to see if a measurement area is occupied by a person (e.g. by detecting motion within the measurement areas) and, in case a measurement area is occupied, to focus on said measurement area for obtaining image data.

Figure 6:
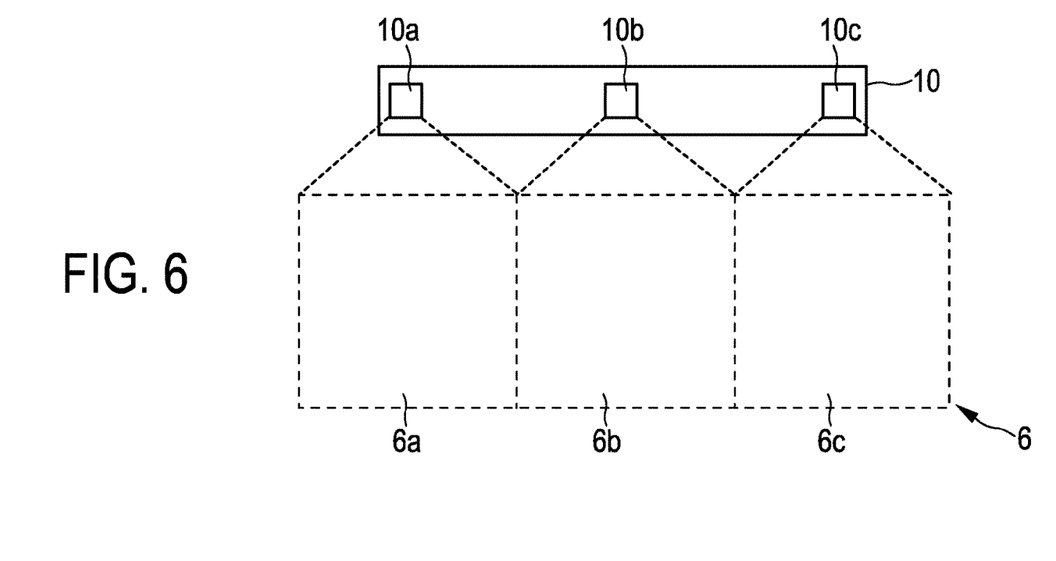
FIG. 6 shows a diagram illustrating the monitoring of a monitored area.

Another scenario for use of the embodiment of the data administration system 1c shown in FIG. 4 is depicted in FIG. 6. In this embodiment the sensor unit 10 is adapted for obtaining image data from a predetermined monitored area 6 for enabling the tracking of a living being in said monitored area 6. For instance, if a patient walks around in a hospital, by use of a plurality of sensors 10a, 10b, 10c that are arranged such that each sensor 10a, 10b, 10c monitors a certain monitored sub-area 6a, 6b, 6c tracking of the patient is easily possible. In addition, in case a person is detected in a certain monitored sub-area image data may be obtained that also allows the extraction of vital signs and features useful for identification of the person.

In the embodiment shown in FIG. 4 the data administration system 1c additionally comprises a notification unit, which may be a monitor for displaying the vital signs together with the identity of an identified person. In another embodiment the vital signs may be sent together with the identity to a predetermined address, such as an emergency center or a mobile device, for instance, if a nurse or doctor wants to follow remotely the vital signs of a particular patient.

Still further, in the embodiment shown in FIG. 4 the data administration system 1c further comprises an audio sensor 11, such as a microphone, for obtaining audio data of said living being 3. Said audio data may then be used in the identification unit, in addition to the extracted features of the living being, to identify the living being in order to further increase the reliability of the identification.

It should be noted in this context that the various optional elements shown in the different embodiments of the data administration system of the present invention depicted in FIGS. 1, 2 and 4 can also be used in other combinations and not necessarily only in the particular combinations as shown in these figures.

An exemplary scenario for use of the present invention in a hospital may be as follows. If a new patient arrives in bed, the proposed system detects that the patient is not enrolled in the system yet and notifies a nurse. Tracking of the patient, in particular for vital signs extraction, is done in an anonymous EHR (electronic health record) giving this new patient a virtual identity (e.g. John Doe 124). After a nurse has enrolled the new patient, the patient's face and the bed location are coupled to the associated EHR, and the anonymous EHR is merged with the patient permanent EHR.

If the patient leaves the bed, the proposed system detects this and administrates it in the system so that, for instance, a nurse can look up who is in bed and who is out of bed. Optionally, the system tracks the user through the hospital using a camera-hand-over. Further, the system optionally notifies a nurse.

If a person enters the bed at a certain location the system checks if the patient is still the same. If this is the case, this patient is continued to be monitored (for vital signs), and the system record for this patient is further updated. If it is identified that the patient is no longer the same, a nurse may be notified. Further tracking (for vital signs) is then done again in an anonymous EHR. The nurse can correct the system if the patient is still the same but is incorrectly recognized, e.g. because the head is bandaged or no longer bandaged which was not yet known to the system. Further, the nurse can stop monitoring the previous patient if the bed has been re-assigned to a different patient. Still further, the nurse can enroll the new patient. If this patient was previously enrolled at a different location in the hospital, the system can be informed that the patient has been moved to a new bed so that now the new patient is tracked at the correct location.

Another scenario for use of the present invention in an emergency ward may be as follows. If a new patient arrives in the waiting room and sits down in a monitored chair the system detects the new patient, starts tracking and stores the obtained vital signs in an anonymous EHR. Optionally, these vital signs are provided to a warning system, such as a system employing EWS-lite (early warning score). If this warning system indicates that certain thresholds are exceeded, immediate attention is needed so that a nurse or a doctor may be warned, including the chair number and a good picture of the face in the warning.

When the patient is registered at the desk, the nurse identifies the patient and the system merges the anonymous EHR with the patient EHR. If the patient continues waiting, the system continues to monitor the patient now using the patient EHR. If the patient is moved into the hospital, the above explained scenario for use of the present invention in a hospital may be relevant. Optionally, the system keeps tracking the patient anywhere in the hospital.

The present invention enables a medically acceptable record-keeping of patient data and reliably avoids the confusion of vital signs parameters of patients which in an extreme case could have a lethal outcome. Further applications of the present invention are all situations where one or more unknown living beings are monitored, such as the waiting room of a veterinarian, a security area, public areas, entrance areas of buildings, etc.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A data administration system comprising:
   at least one video camera for remotely obtaining image data of at least a body part of a living being,
   a photoplethysmography (PPG) device configured to extract one or more vital signs of said living being from the remotely obtained image data of said living being; and
   at least one processor programmed to:
      detect one or more image areas within the images of said image data, an image area covering an area of the size of one or more body parts of a single living being or a complete living being;
      extract one or more features of one or more body parts of said living being from the remotely obtained image data of said living being,
      determine the identity of said living being by use of said one or more extracted features of said living being, and
      associate the one or more extracted vital signs of said living being with the determined identity of said living being.

2. The data administration system as claimed in claim 1, further comprising a storage for storing a database of identities of living beings including one or more features of said living beings,
   wherein the at least one processor is programmed to determine the identity of said living being by comparison of said one or more extracted features of said living being with the features stored in said database of identities.

3. The data administration system as claimed in claim 2, wherein said storage is configured to store said one or more extracted vital signs of said living being in a database entry of the determined identity.

4. The data administration system as claimed in claim 1, wherein said at least one video camera is configured to obtain the image data in the visual and infrared wavelength ranges; and
   said PPG device is configured to extract said one or more vital sings in the visual and the infrared wavelength ranges.

5. The data administration system as claimed in claim 1, wherein said at least one video camera is configured to obtain image data from one or more predetermined measurement areas, a measurement area covering an area of the size of one or more body parts of a single living being or a complete living being, in particular to obtain image data from only those measurement areas including a body part of a living being.

6. The data administration system as claimed in claim 1, wherein the at least one processor is programmed to determine one or more regions of interest of said living being and to extract one or more vital signs from said one or more regions of interest.

7. The data administration system as claimed in claim 1, wherein the at least one processor is programmed to extract one or more features of said living being from the remotely obtained image data of said living being by at least one feature extraction method out of a group of feature extraction methods including:
   i) an object recognition method for recognizing features from face, chest or other body parts,
   ii) a biometric feature extraction method for extracting biometric features, in particular height, width, body contour, body volume,
   iii) a gate analysis method for gate pattern recognition,
   iv) a texture recognition method for recognizing texture features,
   v) a color recognition method for recognizing color features.

8. The data administration system as claimed in claim 1, wherein said at least one video camera comprises a plurality of video camera for obtaining image data from a predetermined monitored area for allowing the tracking of living beings in said monitored area.

9. The data administration system as claimed in claim 1, further comprising a microphone for obtaining audio data of said living being,
   wherein the at least one processor is programmed to determine the identity of said living being by use of said one or more extracted features and the obtained audio data of said living being.

10. A data administration method comprising the steps of:
    with at least one video camera, remotely obtaining image data of at least a body part of a living being,
    with a photoplethysmograph (PPG) device, extracting one or more vital signs of said living being from the remotely obtained image data of said living being,
    with at least one processor, extracting one or more features of said living being from the remotely obtained image data of said living being,
    with the at least one processor, determining the identity of said living being by use of said one or more extracted features of said living being, and
    with the at least one processor, associating the one or more extracted vital signs of said living being with the determined identity of said living being.

11. A processing method for use in a data administration system comprising the steps of:
    with a photoplethysmograph (PPG) device, extracting one or more vital signs of a living being from remotely obtained image data of said living being,
    with at least one processor, extracting one or more features of said living being from the remotely obtained image data of said living being,
    with the at least one processor, determining the identity of said living being by use of said one or more extracted features of said living being, and
    with the at least one processor, associating the one or more extracted vital signs of said living being with the determined identity of said living being.

12. A non-transitory computer-readable medium storing program code means for causing a computer to carry out the steps of the method as claimed in claim 11 when said computer program is carried out on the computer.

13. The method of claim 10, further including:
    detecting one or more image areas within images of said image data, an image area covering an area of the size of one or more body parts of a single living being or a complete living being.

14. The method of claim 10, further including:
obtaining audio data of said living being; and
determining the identity of said living being by use of said one or more extracted features and the obtained audio data of said living being.

15. The method of claim 11, further including:
detecting one or more image areas within images of said image data, an image area covering an area of the size of one or more body parts of a single living being or a complete living being.

16. The method of claim 11, further including:
obtaining audio data of said living being; and
determining the identity of said living being by use of said one or more extracted features and the obtained audio data of said living being.

* * * * *